(12) United States Patent
Williams

(10) Patent No.: US 11,147,477 B2
(45) Date of Patent: Oct. 19, 2021

(54) FALL MANAGEMENT BED PAD

(71) Applicant: Steven Alfred Williams, Kwai Chung (CN)

(72) Inventor: Steven Alfred Williams, Kwai Chung (CN)

(73) Assignee: Rondish Company Limited, Kwai Chung (HK)

( * ) Notice: Subject to any disclaimer, the term of this patent is extended or adjusted under 35 U.S.C. 154(b) by 70 days.

(21) Appl. No.: 15/415,525

(22) Filed: Jan. 25, 2017

(65) Prior Publication Data

US 2017/0209076 A1 Jul. 27, 2017

Related U.S. Application Data

(60) Provisional application No. 62/286,775, filed on Jan. 25, 2016.

(51) Int. Cl.
*A61B 5/11* (2006.01)
*A61B 5/00* (2006.01)
*A61G 7/05* (2006.01)

(52) U.S. Cl.
CPC .......... *A61B 5/1115* (2013.01); *A61B 5/6892* (2013.01); *A61B 5/746* (2013.01); *A61G 7/05* (2013.01); *A61G 2203/34* (2013.01); *A61G 2203/70* (2013.01)

(58) Field of Classification Search
CPC ..... A61B 5/1115; A61B 5/6892; A61B 5/746; A61G 7/05; A61G 2203/34; A61G 2203/70
See application file for complete search history.

(56) References Cited

U.S. PATENT DOCUMENTS

| | | | | |
|---|---|---|---|---|
| 4,175,263 A | * | 11/1979 | Triplett | A61B 5/1115 340/573.4 |
| 5,184,112 A | * | 2/1993 | Gusakov | A61B 5/1115 340/573.1 |
| 5,844,488 A | * | 12/1998 | Musick | G08B 21/22 340/573.4 |
| 9,693,592 B2 | * | 7/2017 | Robinson | A41D 1/005 |
| 2011/0279276 A1 | * | 11/2011 | Newham | A61B 5/1115 340/573.4 |
| 2013/0328574 A1 | * | 12/2013 | Chiou | A61B 5/6892 324/649 |
| 2014/0026682 A1 | * | 1/2014 | Liu | G01L 1/20 73/862.637 |
| 2014/0090489 A1 | * | 4/2014 | Taylor | G01L 1/00 73/862.626 |

(Continued)

*Primary Examiner* — Matthew Kremer
*Assistant Examiner* — Samuel C Kim
(74) *Attorney, Agent, or Firm* — Mintz Levin Cohn Ferris Glovsky and Popeo, P.C.

(57) ABSTRACT

A sensor bed pad has a plurality of layers including an outermost layer made of a flexible material and a pair of inner layers, wherein each inner layer has an electrically conductive material thereon. A central layer is positioned between the pair of inner layers, wherein the inner layers are made of cloth, and wherein the central layer has a plurality of openings extending therethrough. The electrical conductive material of one of the inner layers contacts the electrical conductive material of the other inner layer through the openings in the central layer when a force is applied to the sensor bed pad to complete an electrical circuit between the inner layers.

8 Claims, 6 Drawing Sheets

(56) References Cited

U.S. PATENT DOCUMENTS

| | | | | |
|---|---|---|---|---|
| 2015/0164238 A1* | 6/2015 | Benson | ............... | G16H 50/30 |
| | | | | 340/540 |
| 2017/0020438 A1* | 1/2017 | Wang | ................. | A61G 7/057 |
| 2017/0089775 A1* | 3/2017 | Hsu | ......................... | G01L 1/16 |

* cited by examiner

FALL MANAGEMENT BED PAD

REFERENCE TO PRIORITY APPLICATION

This application claims priority benefit under 35 U.S.C. § 119(e) of U.S. Provisional Patent Application Ser. No. 62/286,775, filed Jan. 25, 2016, and entitled "Fall Management Bed Pad." The priority of the filing date of Jan. 25, 2016 is hereby claimed, and the disclosure of the provisional patent application is hereby incorporated by reference in its entirety.

BACKGROUND

Traditional bed pads used in fall management are typically made of two Polyethylene terephthalate (PET) plastic (rigid) layers separated by a sponge layer and sealed inside an outer PVC layer. A silver or carbon based conductive ink solution is printed onto each PET layer with a silk screen and then baked in over to make the ink hard. The conductive ink of these two layer make contact with one another when weight is applied to the pad (such as the weight of a human body) so as to complete an electrical circuit. If this weight is removed the contact between the layers is lost. The foregoing is the basis of the how the bed pad product detects someone leaving the bed.

These types of pads come with several disadvantages. For example, they can be uncomfortable to lay on as they are quite rigid particularly due to the plastic layers. The bed pads are difficult to keep clean as they cannot be washed and typically cannot be folded due to the rigidity so they are difficult to transport and store. They also can make a distracting noise when the patient moves and are relatively expensive to make, as the manufacturing process involves a lot of labor. The bed pads are also an environmental hazard because they use a lot of plastic and silver based materials.

SUMMARY

In view of the foregoing, there is a need for bed pads that improve upon the aforementioned disadvantages.

In one aspect, there is disclosed a sensor bed pad comprising: a plurality of layers including an outermost layer made of a flexible material, a pair of inner layers, each inner layer having an electrically conductive material thereon, and a central layer positioned between the pair of inner layers, wherein the inner layers are made of cloth, and wherein the central layer has a plurality of openings extending therethrough and wherein the electrical conductive material of one of the inner layers contacts the electrical conductive material of the other inner layer through the openings in the central layer when a force is applied to the sensor bed pad to complete an electrical circuit between the inner layers.

The details of one or more variations of the subject matter described herein are set forth in the accompanying drawings and the description below. Other features and advantages of the subject matter described herein will be apparent from the description and drawings, and from the claims.

DETAILED DESCRIPTION

In view of the foregoing, there is a need for improved bed pads. In an embodiment disclosed herein is a cloth based bed pad with a sensor for sensing whether a patient is located on the pad. The bed pad has a relatively efficient and straightforward manufacturing process. Cloth based sensors have been used in the case of enuresis detection but not for bed exit designs, so a challenge is a bed pad with a fabric based exit alarm pad.

The improved bed pad is flexible, comfortable and virtually unnoticed by the user when on the pad. The bed pad is also washable and therefore easy to keep clean and hygienic. Advantageously, the bed pad is foldable to a small size for easy transport and storage and is relatively silent when in use. The bed pad is low cost and easy to produce with minimum plastics or heavy metals involved in its manufacture.

Figure 1:
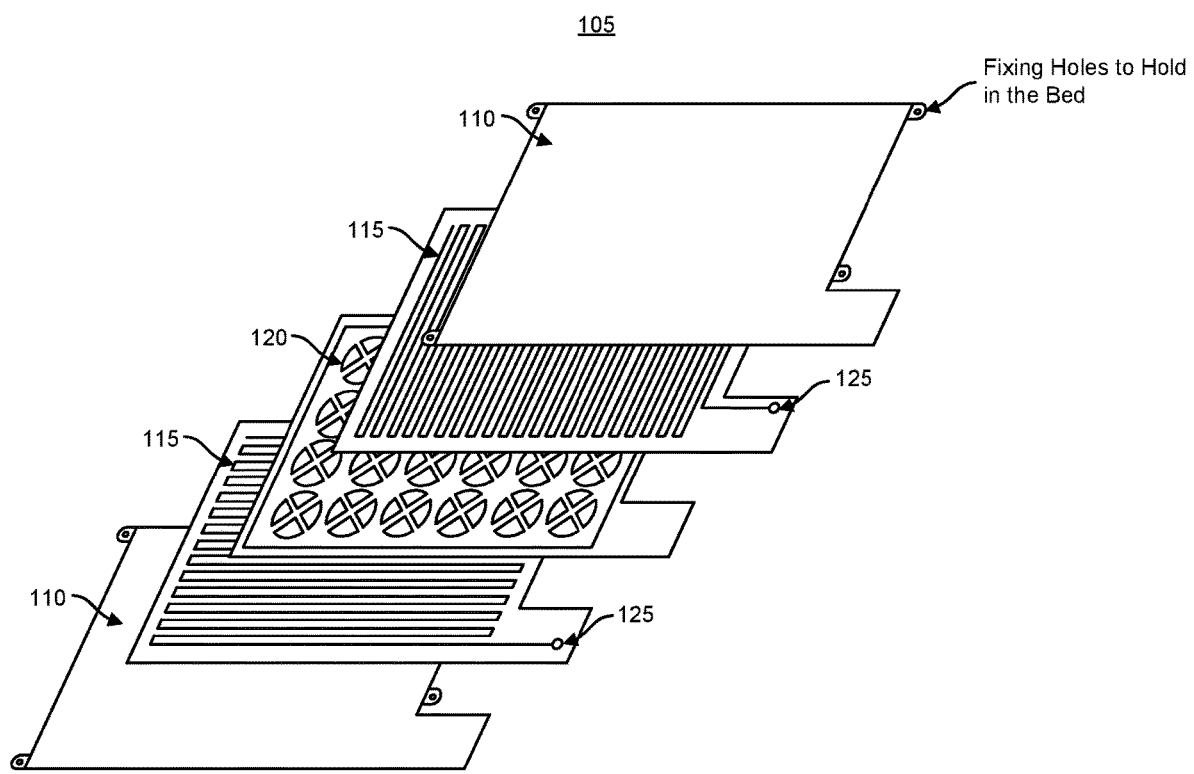
FIG. 1 shows an exploded view of a first embodiment of a bed pad showing layers of the bed pad.

Disclosed herein are two embodiments of a bed pad is formed of multiple layers juxtaposed with one another so as to form a multilayered bed pad. The embodiments are just examples and are not intended to be limiting. FIG. 1 shows a first embodiment of a sensor bed pad. FIG. 1 shows exemplary layers that can be laid atop one another to form the sensor bed pad 105. The bed pad 105 includes a metallic thread woven configuration in that at least one of the layers is formed of a fabric or cloth. This embodiment uses stainless steel, metallic, or other thread that is electrically conductive. The thread is woven into one or more (such as two) layers of cloth (such as linen or other material) to achieve the conductivity. A soft layer with strategically placed holes is fitted between the two layers. When pressure is applied such as when a patient lays on the pad, the two layers of electrically conductive thread make contact with one another through the holes in order to complete an electrical circuit that can be used to generate a signal, such as an alarm. Optionally, an outer layer of linen or other material may be sewn on if required to hide the metallic thread.

Figure 6:
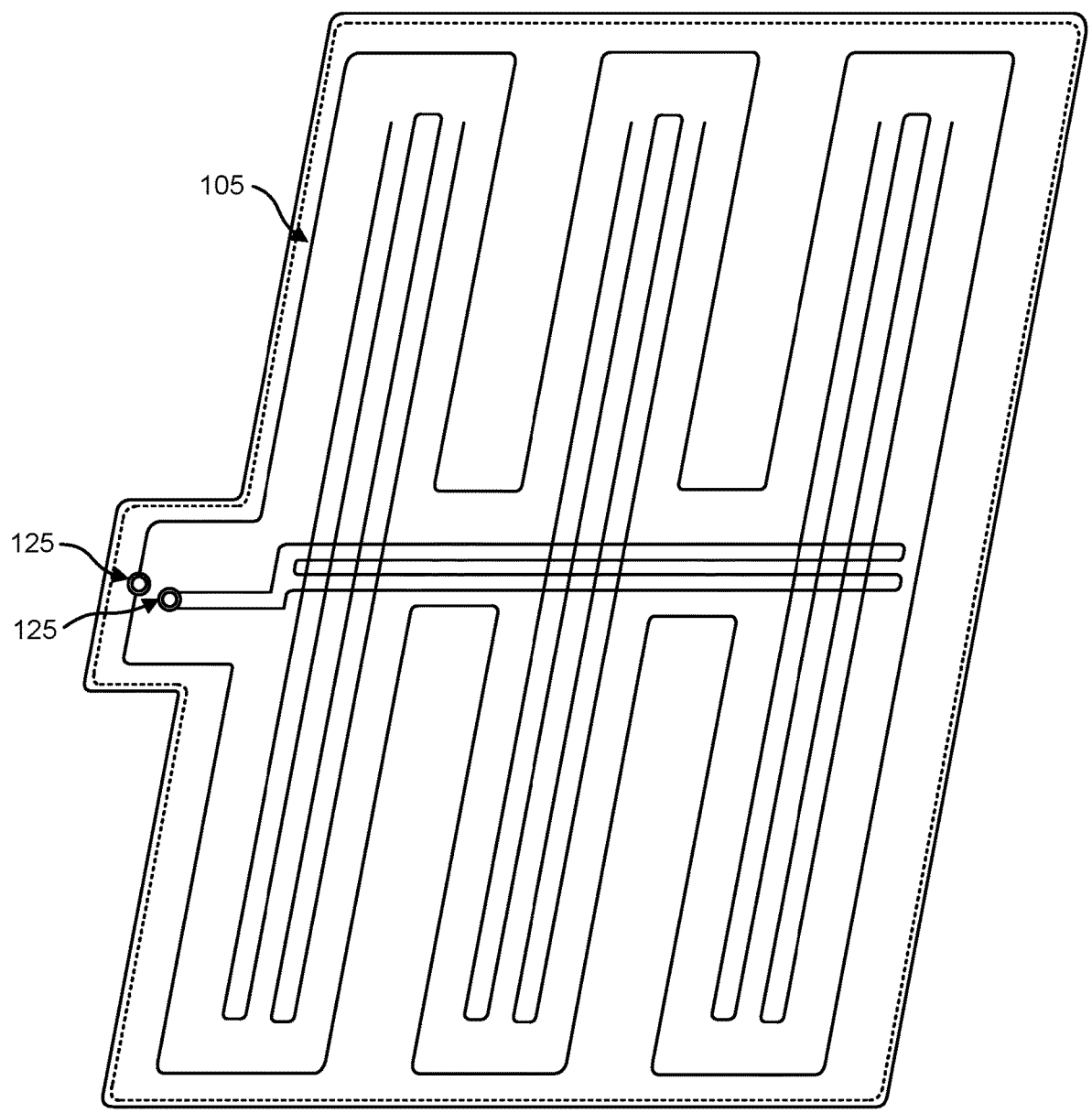
FIG. 6 shows an example bed pad.

FIG. 1 shows example layers of the bed pad 105. FIG. 6 shows an example bed pad 105. A pair of outermost layers 110 collectively forms the outer surfaces of the pad 105. The outermost layers 110 are made of a flexible, soft cloth, linen or other soft material. The outermost layers 110 can include one or more coupling elements, such as holes, eyelets, or openings that can be used to secure the sensor pad to an object such as a bed.

An inner layer 115 is positioned adjacent and inside each of the outermost layers 110. The inner layers 115 collectively form a pair of layers and are each made of a flexible cloth, such as linen, cotton, polyester, etc. A metallic, electrically conductive thread is sewed into, woven into or otherwise embedded or attached to the cloth of each of the inner layers 115. The conductive thread is woven to form a pattern that define the lines of an electrical circuit through which electricity (i.e., an electric current) may pass. In this manner, the inner layers 115 essentially form one or more electrical circuit layers with the circuits lines or traces being defined by the electrically conductive thread that is woven into the cloth of the to the inner layers 115. The metallic thread can be interwoven during manufacture of the sensor pad, such as at the factory, to the required pattern. Thus, according to a method of manufacture, a metallic thread (or any electrically conductive thread or filament) is woven into a flexible layer of material to form one or more traces or lines of a circuit.

With reference still to FIG. 1, a center layer 120 is positioned between the two inner layers 115. The center layer 120 is flexible as are all of the other layers. The center layer may serve at least partially as a padding layer and can add a layer of comfort to the bed pad. In an embodiment, the center layer 120 is made of a soft material, such as cloth, sponge, foam, etc. The center layer has a plurality of openings or holes that extend through the center layer. The holes provide a conduit through which the inner layers 115 can contact one another when a force is applied to the bed pad 105, such as when a patient sits on or lays on the bed pad 105.

The force can be sufficient to cause the flexible inner layers 115 to deformably and malleably move toward one another or to cause one of the inner layers 115 to move toward the other inner layer. When this occurs, the metallic threads on one of the inner layers 115 can contact the metallic threads of the other inner layer 115 such that the contact creates and completes an electrical circuit, which can be an indication that the patient is on or is no longer on the bed pad. An electrical signal or other type of signal can then be emitted in the form of alarm.

In the completed sensor pad, the outer, peripheral edges of the outermost layers can be fitted and connected to one another, such as through sewing pursuant to a method of manufacture. In this manner the outermost layers collectively form an interior cavity in which the other layers are positioned such that the layers are juxtaposed flatly against one another within the outermost layers. At the edge of the material of the inner layers 115, one or more connectors 125 are fitted or attached and a tight reliable connection made for a cable or a wireless (such as RF) transmitter/transceiver. Any of the embodiments of the sensor pad described herein can include connectors in the form of a coupling mechanism such as a wired or wireless coupling mechanism for communicatively and/or electrically coupling the sensor pad to a communication device and/or a source of power. The communication device can be any type of communication device and can include a speaker, a transmitter, a receiver, etc.

As mentioned, in any of the embodiments the connectors can be snap-type button connectors such as those used on clothes. The buttons can be detached from one another such as to remove an attached wire or transmitter. When the cable or the transmitter is removed, the pad can be washed.

Figure 2:
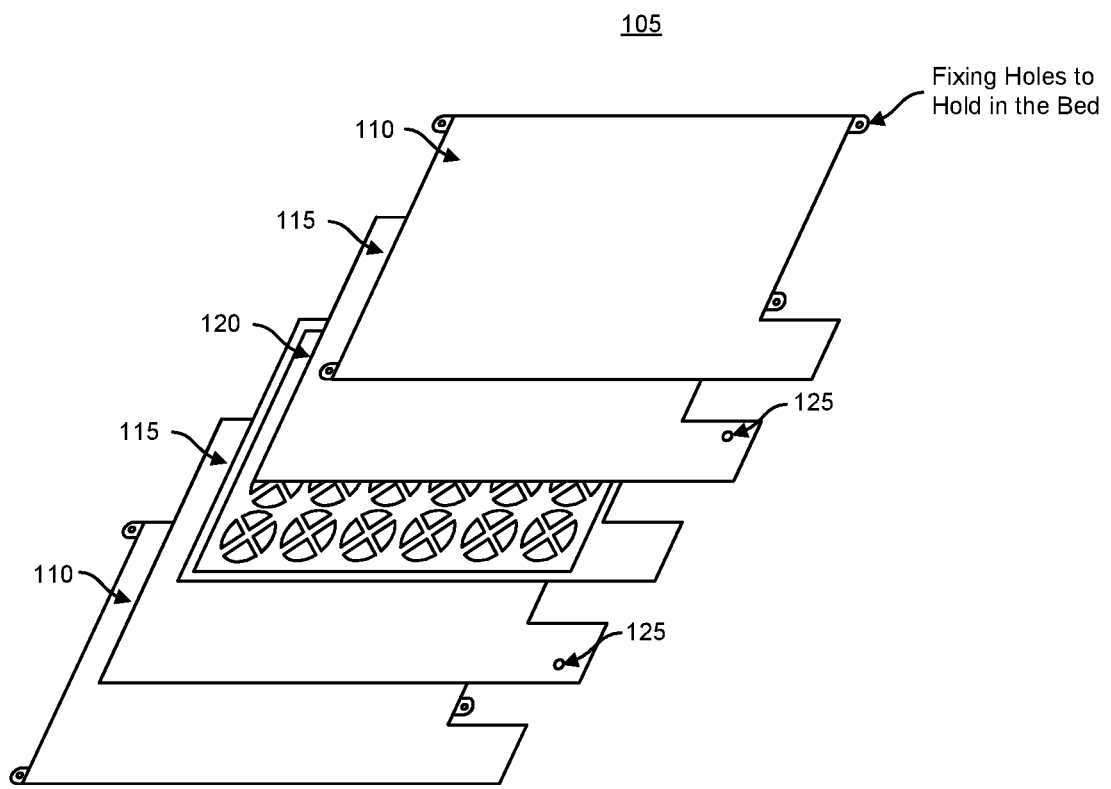
FIG. 2 shows an exploded view of a second embodiment of the bed pad showing layers of bed pad.

FIG. 2 shows another embodiment of the sensor pad 105. This embodiment also includes a pair of optional outer layers 110 that can be the same as or similar to the outer layers in the previous embodiment. A pair of inner layers 115 are positioned adjacent to an between the outermost layers 110. In this embodiment, the inner layers are made of a conductive material such that the entire inner layer is conductive. With respect to the inner layers, the conductive material for which the inner layers are made is commercially available and traditionally used for anti-static clothing or RF shielding such as curtains etc.

The inner layers are a cloth or fabric material such that the inner layers are flexible and not rigid. In this regard, any of the interior layers of the sensor pads described herein are sufficiently flexible that the entire sensor pad is pliable and will be comfortable to a user. None of the layers are sufficiently rigid to dictate a fixed shape or contour for the bed pad.

With reference still to FIG. 2, a soft central layer 120 with strategically placed holes is fitted between the two inner layers 115. As in the previous embodiment, when pressure is applied such as by the patient laying on the pad, the two inner layers 115 make contact with one another through the holes, openings, or apertures of the central layer 120. This completes an electrical circuit that could serve as an indication that a person sitting on, laying on or otherwise a top the bed pad. The pad also includes a connection for cable or RF transmitter/transceiver or other type of communication or electrical connection. A connection point as shown on the diagrams is placed near the edge of the pads and allows either the connection of a cable or a wireless transmitter.

Figure 3:
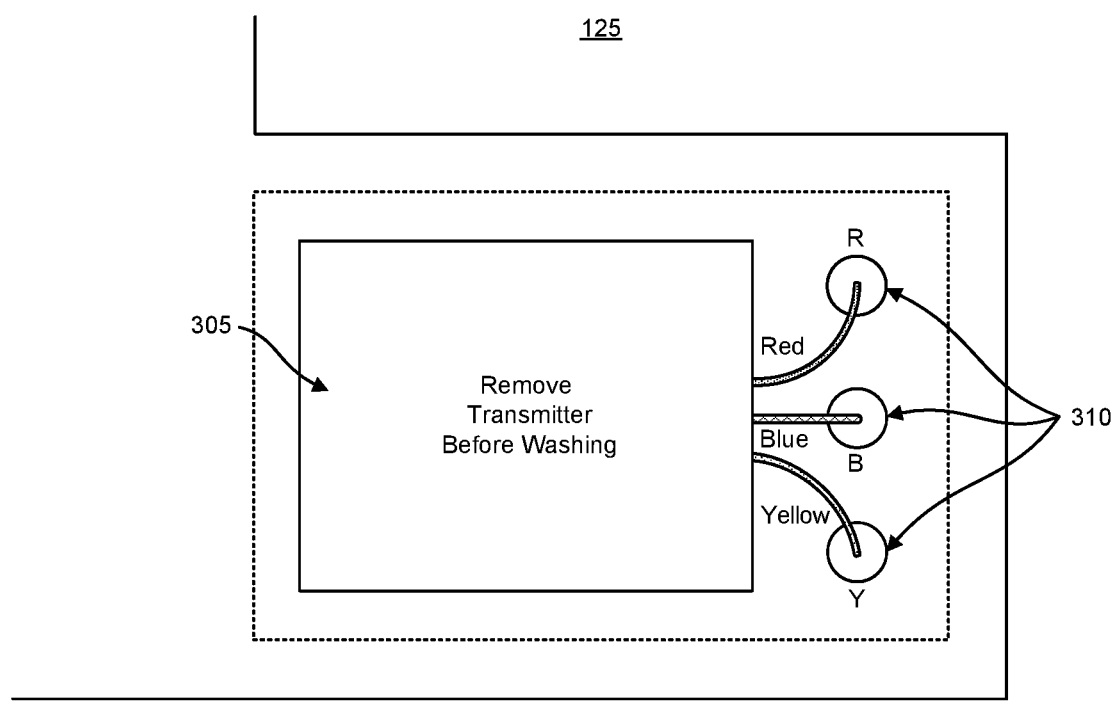
FIG. 3 shows a wireless interface region for a bed pad.
Figure 4:
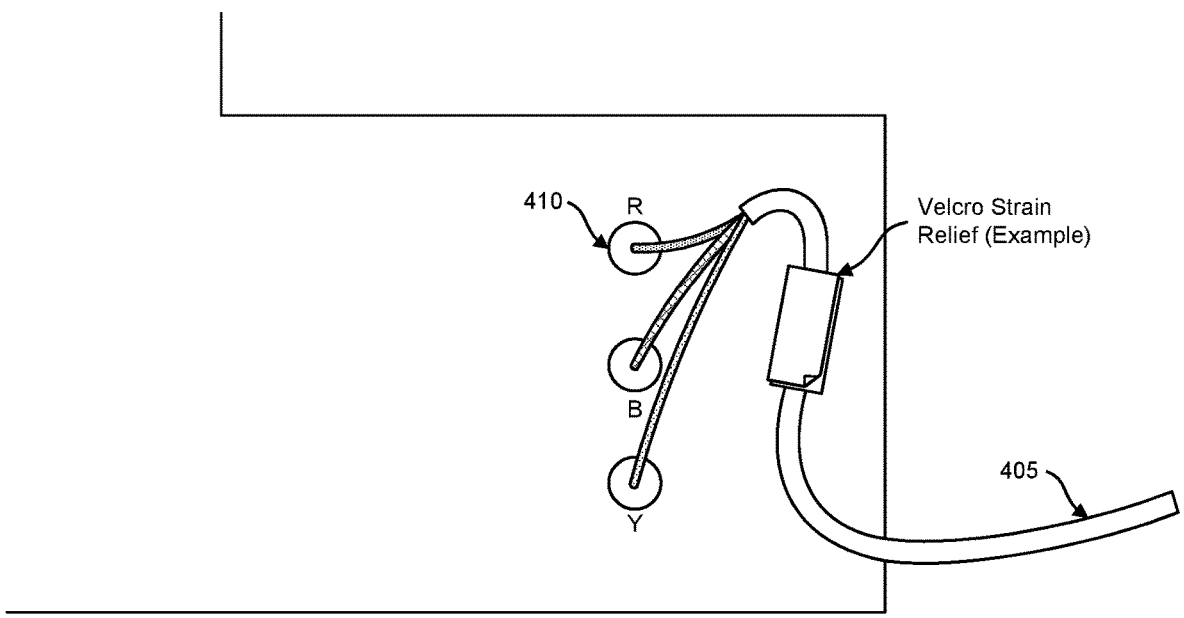
FIG. 4 shows a wired interface region for a bed pad.

The connector 125 can be placed inside the pouch or cavity that is formed by the outermost layers. FIG. 3 shows an example of a wireless connector 125. The wire connector includes a wireless transmitter 305 that can include a label to indicate to the user that the transmitter should be removed prior to watching. The transmitter 305 can be removably connected to one or more electrical interfaces 310, such as via snap type connections. FIG. 4 shows an example of a wired connector region. A cable 405 can be physically connected to one or more electrical interfaces 410 of the sensor pad. The electrical interfaces can be for example snap type connectors that connect to the cable 405. For a cable or wire based version, a strain relief using Velcro can be used for a wired version on the pad. All pads can have fixing hole points to allow in the corners to allow the pad to be tied to the bed.

It should be appreciated that any of a variety of other options can be used. For example a second wire circuit can be placed on and connected to a top region of the pad without making direct connection with any wire. The second wire circuit can be configured to detect a reduction of resistance when a liquid, such as water or urine, is place on or otherwise positioned the pad. The pad therefore has the double function of detecting pressure or weight and water.

Figure 5:
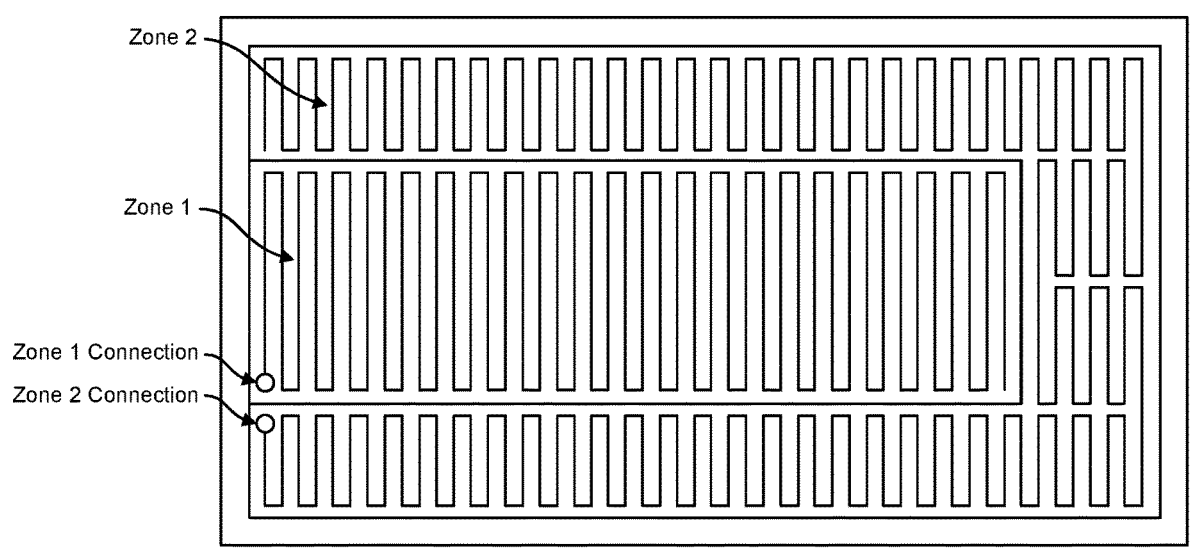
FIG. 5 shows an example of a multi-zoned pad that is configured to detect the patient moving around in the bed.

FIG. 5 shows an example of a multi-zoned pad that is configured to detect the patient moving around in the bed. In an embodiment, two or more electrical circuits are placed and spatially arranged in zones. Each zone can independently detect the presence of a patient on the pad. For example, a first zone can be positioned around the outermost edge of the pad with a second zone positioned in a central region of the pad. If the patient moves to the edge of the pad from the central region of the pad, such a movement position of the patient will be detected by a change in electrical indication from the first zone to the second zone. If the patient stays at the outer edge of the pad there for a predetermined period of time, the bed pad may alert that the patient may be leaving the bed.

The disclosed type of cloth based design lends itself far better to this option than a standard PVC pad design due to it greater flexibility and the fact that it is easier to separate the zones by using thread to have distinct areas.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, methods of use, embodiments, and combinations thereof are also possible. Therefore the spirit and scope of the appended claims should not be limited to the description of the embodiments contained herein.

What is claimed is:

1. A sensor bed pad comprising:
a plurality of layers including a pair of outermost layers made of a flexible material, a pair of inner layers, each inner layer having an electrically conductive material thereon, and a central layer positioned between the pair of inner layers, wherein the inner layers are made of cloth, and wherein the central layer has a plurality of openings extending therethrough and wherein the inner layers are positioned such that the inner layers can move relative to one another and relative to the central layer, and wherein the pair of outermost layers entirely enclose the pair of inner layers and the central layer;
wherein the electrical conductive material of one of the inner layers contacts the electrical conductive material of the other inner layer through the openings in the central layer when a force is applied to the sensor bed pad to form an electrical conduction between the inner layers and complete an electrical circuit between the inner layers, and wherein one of the inner layers moves toward the other inner layer when such force is applied;
and wherein each of the inner layers includes a first zone positioned within a central region of each of the inner layers and a second zone positioned entirely along outermost, opposed lateral edges of the pad, and wherein each of the second zones has a U-shape that defines an interior region and wherein the respective first zone is entirely positioned within the interior region of the U-shape such that each of the second zones at least partially surrounds the respective first zone, and wherein each of the first and second zones contains a single electrical circuit line that spans a respective zone in a zig-zag pattern, and wherein a change in electrical indication from the respective first zone to the respective second zone indicates patient movement along the sensor bed pad.

2. The sensor bed pad of claim 1, wherein at least one of the inner layers is at least partially made of the electrically conductive material.

3. The sensor bed pad of claim 1 wherein the electrically conductive material comprises an electrically conductive thread that is sewn onto the cloth of at least one of the inner layers.

4. The sensor bed pad of claim 3, wherein the electrically conductive thread defines a circuit pattern formed of an elongated line having a first terminal end coupled to a wired or wireless connector and wherein the entire line is formed of the electrically conductive thread sewn onto the cloth of the at least one of the inner layers.

5. The sensor bed pad of claim 1, further comprising a communication interface on the sensor bed pad.

6. The sensor bed pad of claim 5, wherein the communication interface is a wireless interface.

7. The sensor bed pad of claim 5, where the communication interface is a wired interface.

8. The sensor bed pad of claim 1, wherein each of the entire second zones is rectangular.

* * * * *